United States Patent

Devanathan

[11] Patent Number: 5,911,575
[45] Date of Patent: Jun. 15, 1999

[54] BAND MATERIAL, RING BLANK, ORTHODONTIC BAND AND METHOD OF MAKING

[75] Inventor: Thrumal Devanathan, Warsaw, Ind.

[73] Assignee: TP Orthodontics, Inc., Westville, Ind.

[21] Appl. No.: 09/139,490

[22] Filed: Aug. 25, 1998

[51] Int. Cl.[6] .............................. A61C 3/00; B21F 43/00
[52] U.S. Cl. .......................................... 433/23; 29/891.11
[58] Field of Search ........................ 433/23, 9; 29/896.11

[56] References Cited

U.S. PATENT DOCUMENTS 4,840,562  6/1989  Wilson et al. .
5,441,409  8/1995  Tuneberg .

OTHER PUBLICATIONS

Dentaurum ad, *Journal of Clinical Orthodontics,* Aug. 1994 (2 pages).
Catalog of American Orthodontics Corporation, 1985, pp. 1 and 23.

*Primary Examiner*—Jeffrey A. Smith
*Attorney, Agent, or Firm*—Lloyd L. Zickert

[57] ABSTRACT

An orthodontic band having a patterned surface formed with a pattern of indentations for securing the band to a tooth to enhance retention, wherein the patterned surface is formed by a metal displacement operation.

32 Claims, 3 Drawing Sheets

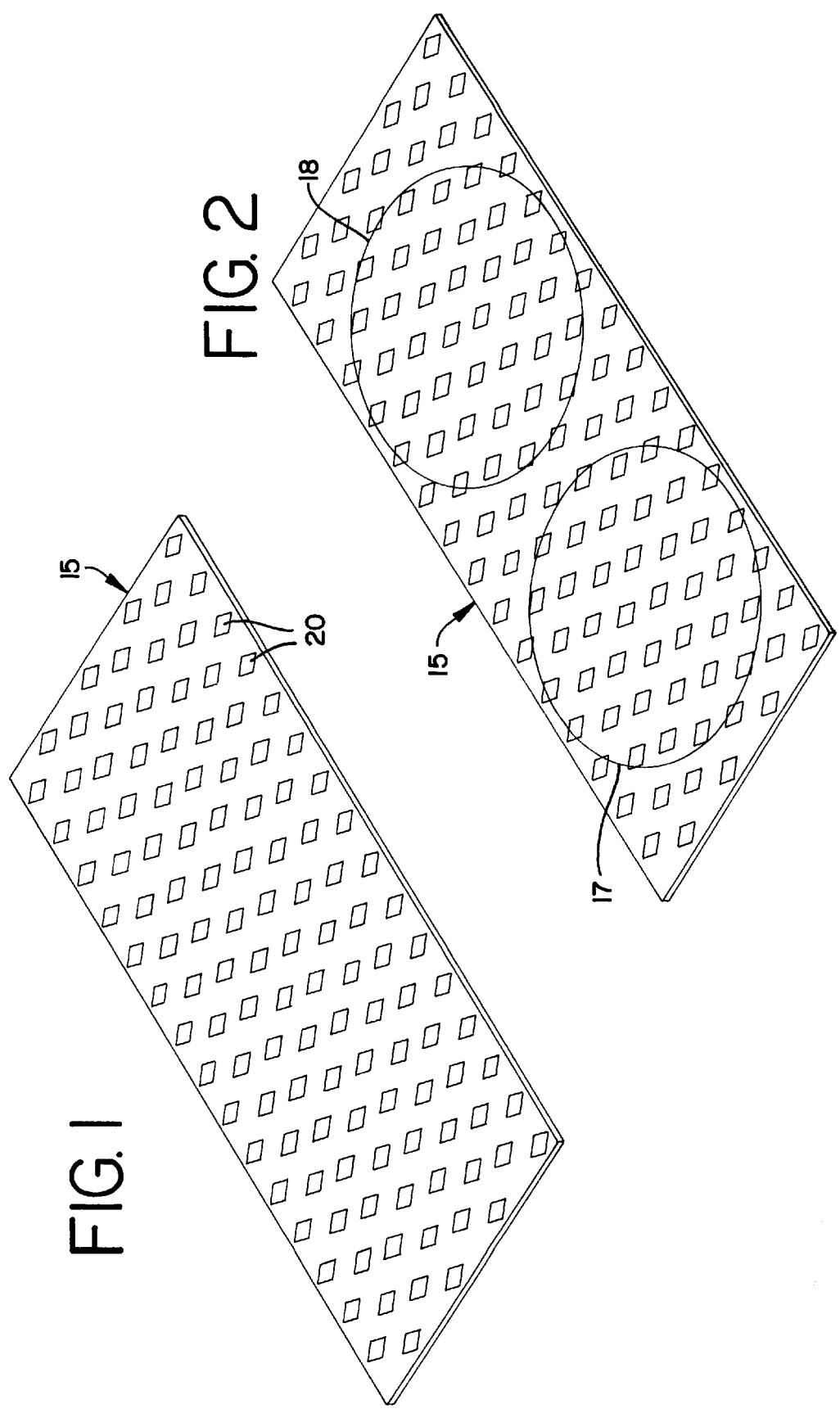

100x

100x

5,911,575

BAND MATERIAL, RING BLANK, ORTHODONTIC BAND AND METHOD OF MAKING

This invention relates in general to an orthodontic band having a surface patterned for enhancing attachment of the band to a tooth surface with a suitable cement, and where the patterned surface includes a plurality of indentations that are formed by a metal displacement procedure.

BACKGROUND OF THE INVENTION

Orthodontic bands are used to mount various orthodontic attachments to a tooth wherein the band encircles the tooth and includes an outer surface on which an attachment may be suitably mounted. A band is secured to a tooth by a suitable cement. It is very important that the integrity of a band be such as to maintain the band mounted in place for at least the period of time that orthodontic treatment is needed.

Various clinical problems result from loose bands, including the need for emergency office visits and the scheduling of extra appointments for the replacement and re-cementing of a band to a tooth.

It has been known to apply metal mesh to the inner surfaces of bands to increase the bondability to a tooth, as disclosed in U.S. Pat. No. 4,840,562. However, the addition of metal mesh increases the thickness of the band at the area of the attachment and further affects the fit of the band on the tooth.

It has also been known to texturize the bonding surface of a band by sandblasting the surface which requires a secondary operation to the band-forming operation that is costly during band manufacture; and it has been known to photo-etch the attaching band surfaces, as disclosed in U.S. Pat. No. 5,441,409. All of these methods of texturizing a surface to enhance bondability are relatively costly and generally tend to reduce band strength by the removal of metal from the band material.

SUMMARY OF THE INVENTION

The present invention involves providing an orthodontic band having a surface patterned to enhance band retention by displacing the metal on the inner or tooth-side surface to form a pattern of indentations or pockets, wherein the metal displacement may be accomplished by the use of a tool, such as a stamping, knurling, or single-point tool. The metal displacement operation is inexpensive, and no metal is removed from the band material, thereby maintaining the strength and rigidity of the band.

The metal-displaced pattern of indentations, with the indentations substantially equally spaced apart, provides a patterned tooth side surface for contact with band cement that is used to secure the band to a tooth.

Accordingly, the present invention provides an improved orthodontic band for the attachment of orthodontic attachments to a tooth.

It is therefore an object of the present invention to provide a new and improved orthodontic band having an inner surface worked and formed by metal displacement that not only enhances the retention of the band on a tooth but also maintains the strength and rigidity of the band.

A further object of the present invention is to provide an orthodontic band for securing attachments to teeth having a cementable or bondable surface that is economically changed by metal displacement through a stamping, knurling, or other metal-displacement procedure.

Another object of the present invention is to provide a new and improved orthodontic band with the attaching surface that has been worked to provide a pattern of indentations formed by metal displacement such as by stamping, knurling, or single-point indentation.

Other objects, features and advantages of the invention will be apparent from the following detailed disclosure, taken in conjunction with the accompanying sheets of drawings, wherein like reference numerals refer to like parts.

DESCRIPTION OF THE DRAWINGS

FIG. 1 is a greatly enlarged perspective view of a sheet or strip of band material that has been subjected to a metal displacement operation according to the invention and showing the pattern of formed indentations;

FIG. 2 is a view like FIG. 1, which also illustrates the cutting of circular blanks to be die-worked to form a ring blank for a tooth band;

DESCRIPTION OF THE INVENTION

Figure 3:
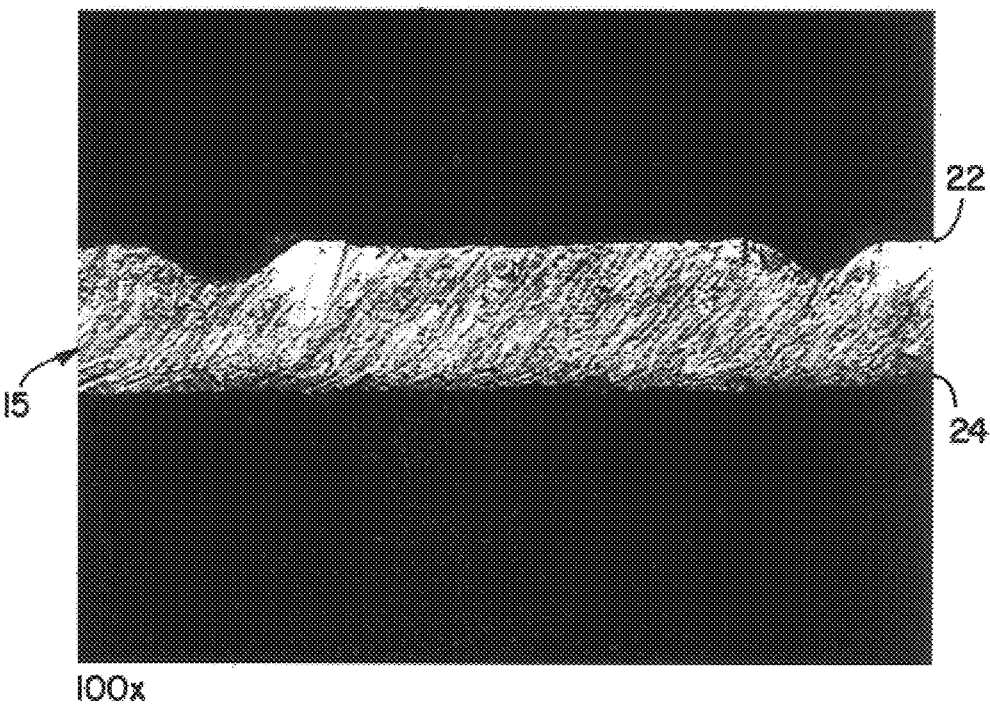
FIG. 3 is a 100× magnification photomicrograph of an end view of a cut through the indentations of a sheet of material having been subjected to a metal-displacement operation according to the invention.

Referring now to the drawings, and particularly to FIGS. 1 to 4, the metal banding material of the invention used to form the orthodontic bands of the invention is initially in sheet or strip form, as shown by the sheet 15 in FIG. 1. The metal is of a suitable stainless steel such as in the 300 series, and of a thickness of about 0.005 to 0.0075 inch. The band material shown in FIGS. 1 to 4 is about 0.0075 inch thick. The sheet is subjected to a metal displacement operation according to the invention to form indentations 20 in a suitable pattern and shape. The width of the sheet 15 and length is sufficient so that a plurality of circular ring blanks can be cut from the sheet. As illustrated in FIG. 2, ring blanks 17 and 18 have been cut from the sheet 15.

Figure 4:
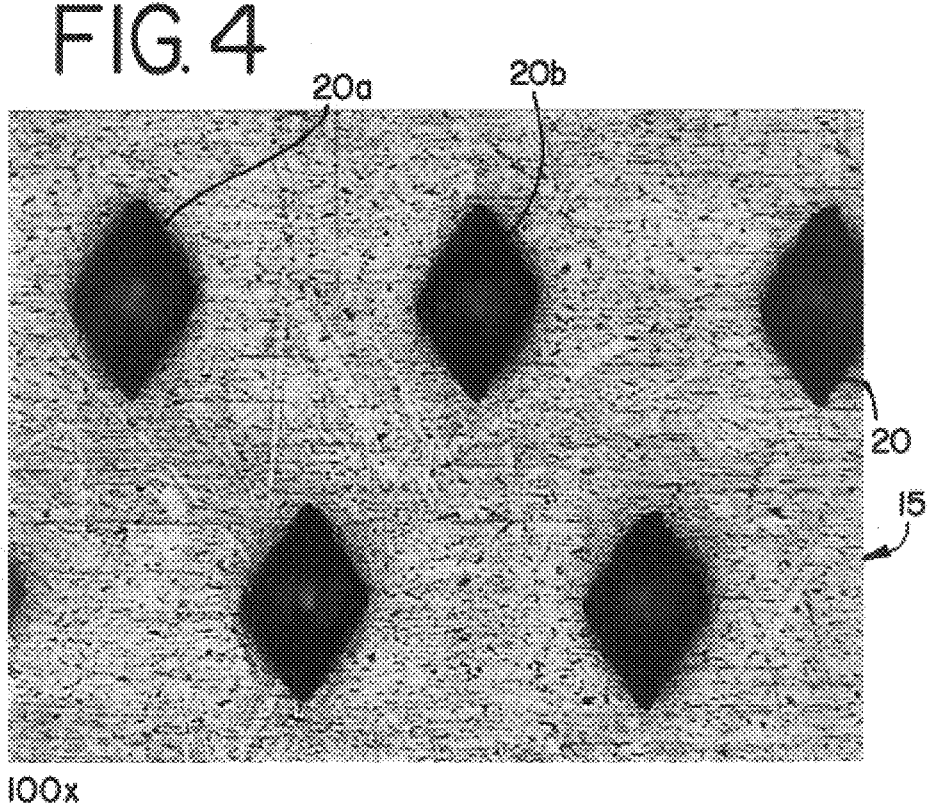
FIG. 4 is a 100× magnification photomicrograph of a plan view of a sheet of material and illustrating the pattern of indentations formed according to the invention.

As seen in FIG. 4, a photomicrograph of a portion of a sheet of material formed according to the invention illustrates the formation of rows of diamond-shaped indentations 20 that are arranged in staggered relation from one row to the next. It may be appreciated that the indentations may be in aligned relation from one row to the next. Preferably, the indentations, when diamond-shaped as shown, are substantially equally spaced apart in any suitable pattern, as seen in FIG. 4.

The indentations made on one surface of the sheet 15, which will become the attaching or tooth side surface of the band, may be made by stamping the sheet with a suitable roller or plate die or by feeding the sheet through a knurler or knurling roller made of a pair of opposed rollers, one of which would have a patterned die to form the pattern of indentations and the other of which would have a smooth surface. A single-point indentation tool or die may also be used to form the indentations. Thus, any suitable metal-displacing indentation tool may be used to form the pattern of indentations.

While the spacing and depth of the indentations may be varied, a suitable spacing between the edges of adjacent indentations along a row, such as indentations 20a and 20b, would be about 0.008 inch. The spacing between adjacent rows would be about 0.004 inch. Thus, the spacing on a horizontal axis between the tips of indentations 20a and 20b, as seen in FIG. 4, would be about 0.008 inch, while the spacing on a vertical basis between the tips of one row and the indentation tips of an adjacent row would be about 0.004 inch. This pattern provides substantially equal spacing between all indentations whereby the strength and rigidity of the band material is substantially the same in any direction. Preferably, the diamond-shaped indentations are oriented with respect to each other, as seen in FIG. 4. Also, where the thickness of the band material would be about 0.0075 inch, the depth from the indentation side of the sheet to the bottom of the indentation would be about 0.0015 inch.

It will be understood that both sides of the strip of material prior to being subjected to a metal displacement operation will be smooth. The side of the strip, generally designated by the numeral 22, having the indentation pattern may be referred to as the metal-displacement side or the indentation side, as shown in FIG. 3. This side ultimately becomes the tooth side of a band. The opposite side, which will be smooth after the metal-displacement operation, may be referred to as the non-indentation side or the smooth side 24 and onto which a suitable orthodontic attachment may be mounted.

Figure 5:
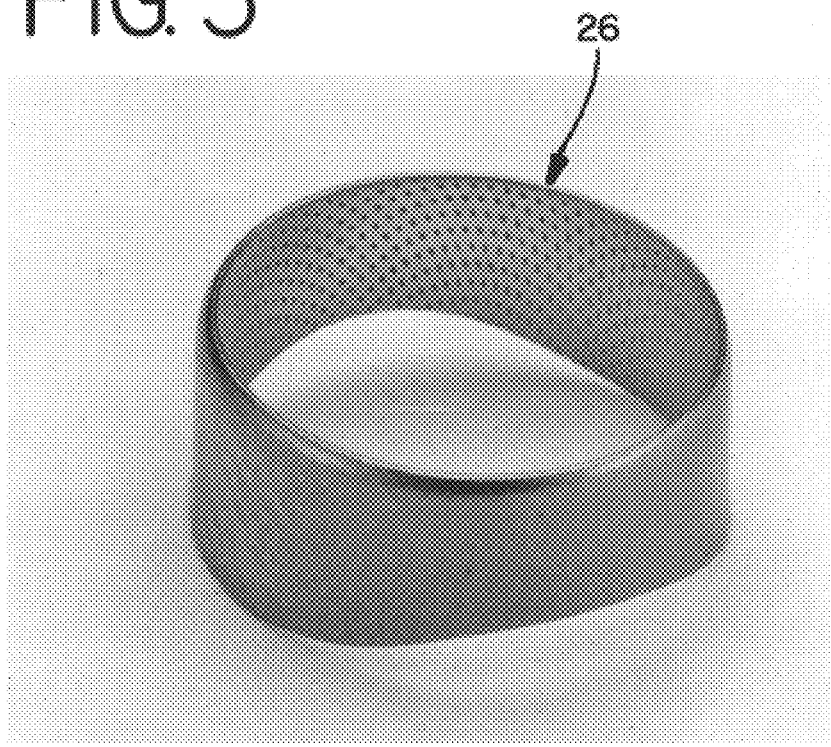
FIG. 5 is an enlarged photograph of a ring blank made from a circular blank of the band material according to the present invention.

Once the strip of material 15 has been subjected to a metal displacement operation, ring blanks 17 and 18 are cut from the strip and each ring blank then is subjected to additional die-forming steps in a well known manner to die-work the ring blank into a hat-shaped form. The ring blank will be put through a series of punch dies having close tolerances. When the die-working operation has been completed, the flat end wall will be cut off to thereafter define a ring blank 26, as shown in FIG. 5.

Figure 6:
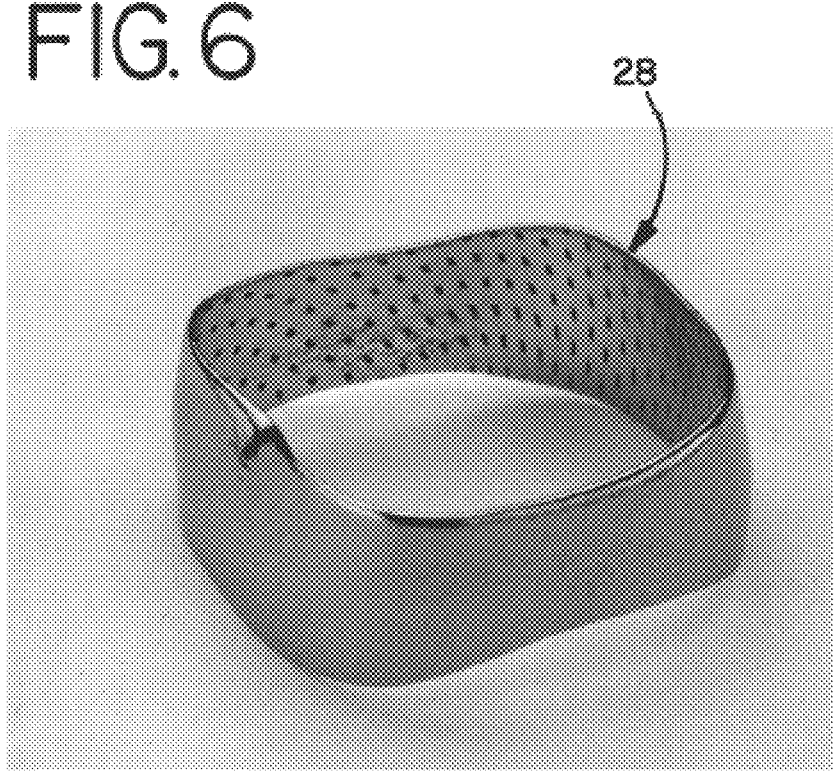
FIG. 6 is an enlarged photograph of a completed band made from a ring blank with an indented inner surface.

The ring blanks are thereafter subjected to additional die-forming steps in order to form an anatomically shaped bracket to fit a particular tooth. During the die-working of the circular blank to form the ring blank 26, the indentation pattern may become somewhat changed. Further, additional die-forming steps to anatomically shape the band may further change the form of the indentations and the pattern. A completed band according to the present invention is illustrated in FIG. 6 and designated by the numeral 28. This band having the inner or tooth-side surface formed with the metal displaced indentation pattern will enhance the retention of the band to a tooth when the band is secured to a tooth with a suitable band cement. It will also be appreciated that the ring blank 26 and the band 28 are seamless and of the type that is preferred for use in the banding of a tooth with a suitable orthodontic attachment. Thus, as shown in FIGS. 5 and 6, the exterior surface of the band is smooth and on which a desired attachment, such as a buccal and/or headgear tube, a bracket, or a hook, may be suitably secured such as by welding, while the internal surface that would engage the outer surface of a tooth includes the metal displaced indentation pattern that coacts with the adhesive or cement to enhance the retention of the band to a tooth.

It will be appreciated that the size of the ring blank may be varied depending upon the tooth on which the ring blank is to be mounted. Further, the size of the completed band may even be changed from that of the ring blank because of the additional die-working steps needed for anatomically shaping the band. Accordingly, a suitable band material of a desired thickness, such as 0.0075 inch, of a suitable stainless steel will be used to make the band of the present invention.

It will be appreciated that the shape of the indentations may be of any suitable polygonal shape, circular in form or cone shaped, and be in accordance with the present invention. As particularly shown in FIG. 3, the diamond-shaped indentations form sloping walls in the banding material from each of the corners of the diamond down to the bottom of the indentation. This formation will substantially increase the area for receiving the cement or adhesive to thereby enhance the retention of the band while avoiding the removal and loss of metal from the band that would reduce the strength and rigidity of the band.

From the foregoing, it can be appreciated that the band of the invention may be economically made, and will enhance retention on a tooth while maintaining the strength and rigidity of the band.

It will be understood that modifications and variations may be effected without departing from the scope of the novel concepts of the present invention, but it is understood that this application is to be limited only by the scope of the appended claims.

The invention is hereby claimed as follows:

1. A metal band material adapted to make ring-shaped orthodontic bands, said material being in flat sheet or strip form and of a thickness suitable for die-working, said sheet having a pattern of indentations formed on the side which becomes the inside or tooth-side surface of the band to enhance retention to a tooth, and said indentations being formed by metal displacement.

2. The band material of claim 1, wherein said indentations are substantially equally spaced apart.

3. The band material of claim 1, wherein the metal displaced indentations are formed by stamping the sheet by an indentation-forming tool.

4. The band material of claim 1, wherein the metal displaced indentations are formed by feeding the sheet through knurling rollers.

5. The band material of claim 1, wherein the indentations are polygonally shaped.

6. The band material of claim 1, wherein the indentations are diamond shaped.

7. The band material of claim 1, wherein the indentations are circular shaped.

8. The band material of claim 1, wherein the indentations are cone-shaped.

9. A metal ring blank for making a ring-shaped orthodontic band from a series of dies, said blank being circularly shaped and having a thickness suitable for an orthodontic band, the outer side of the blank being smooth and the inner side being patterned, said patterned side including a plurality of metal displaced indentations.

10. The ring blank of claim 9, wherein the indentations are substantially equally spaced apart.

11. The ring blank of claim 9, wherein the metal displaced indentations are formed by stamping the sheet by an indentation-forming tool.

12. The ring blank of claim 9, wherein the metal displaced indentations are formed by feeding the sheet through knurling rollers.

13. The ring blank of claim 9, wherein the indentations are polygonally shaped.

14. The ring blank of claim 9, wherein the indentations are diamond shaped.

15. The ring blank of claim 9, wherein the indentations are circular shaped.

16. The ring blank of claim 9, wherein the indentations are cone-shaped.

17. A seamless orthodontic band, said band including a smooth outer surface onto which an appliance may be mounted, and a patterned inner surface adapted to be cemented to a tooth, said band being die-worked from metal band material having a smooth surface on one side and a patterned surface on the other side, said patterned surface including a plurality of metal displaced indentations, whereby said patterned surface enhances the retention of the band to a tooth.

18. The band material of claim 17, wherein the indentations are substantially equally spaced apart.

19. The band material of claim 17, wherein the metal displaced indentations are formed by stamping the sheet by an indentation-forming tool.

20. The band material of claim 17, wherein the metal displaced indentations are formed by feeding the sheet through knurling rollers.

21. The band material of claim 17, wherein the indentations are polygonally shaped.

22. The band material of claim 17, wherein the indentations are diamond shaped.

23. The band material of claim 17, wherein the indentations are circular shaped.

24. The band material of claim 17, wherein the indentations are cone-shaped.

25. A method of making a metal seamless orthodontic band ring blank from a circular blank having a smooth surface on one side and a pattern of metal displaced indentations on the other side, which includes the steps of:

providing a sheet of metal with smooth surfaces on both sides, subjecting one side of said sheet to a metal displacement operation to form a pattern of indentations, cutting the sheet to form at least one circular blank, subjecting the circular blank to a plurality of dies to die-work the blank into a hat-shaped form with the patterned surface on the inside and including an annular wall and a flat end wall, and removing the flat end wall.

26. The method of claim 25, wherein the step of forming the pattern of indentations includes the step of substantially equally spacing apart the indentations.

27. The method of claim 25, wherein the step of metal displacement comprises stamping the sheet by an indentation-forming tool.

28. The method of claim 25, wherein the step of metal displacement comprises feeding the sheet through knurling rollers.

29. The method of claim 25, wherein the indentations are polygonally shaped.

30. The method of claim 25, wherein the indentations are diamond shaped.

31. The method of claim 25, wherein the indentations are circular shaped.

32. The method of claim 25, wherein the indentations are cone-shaped.

* * * * *

UNITED STATES PATENT AND TRADEMARK OFFICE
CERTIFICATE OF CORRECTION

PATENT NO.   : 5,911,575
DATED        : June 15, 1999
INVENTOR(S)  : Thrumal Devanathan It is certified that error appears in the above-indentified patent and that said Letters Patent is hereby corrected as shown below:

Col. 2, line 11, after "DESCRIPTION OF THE DRAWINGS" insert the following paragraph:

--The file of this patent contains at least one drawing executed in color. Copies of this patent with color drawing(s) will be provided by the Patent and Trademark Office upon request and payment of the necessary fee.--

Signed and Sealed this

Fourteenth Day of December, 1999

Attest:

*Attesting Officer*

Q. TODD DICKINSON

*Acting Commissioner of Patents and Trademarks*

UNITED STATES PATENT AND TRADEMARK OFFICE
CERTIFICATE OF CORRECTION

PATENT NO. : 5,911,575
DATED : June 15, 1999
INVENTOR(S) : Devanathan et al.

It is certified that error appears in the above-identified patent and that said Letters Patent is hereby corrected as shown below:

Title page,
Item [75], Inventor: Thrumal Devanathan, Warsaw, Ind." to
-- [75] Inventors: Thrumal Devanathan, Warsaw, Ind.; David W. Thornburg, LaPorte, Ind. --

Signed and Sealed this

First Day of July, 2003

JAMES E. ROGAN
*Director of the United States Patent and Trademark Office*